United States Patent [19]

Rattner

[11] Patent Number: 5,393,296
[45] Date of Patent: Feb. 28, 1995

[54] METHOD FOR THE MEDICAL TREATMENT OF PATHOLOGIC BONE

[75] Inventor: Manfred Rattner, Grossenseebach, Germany

[73] Assignee: Siemens Aktiengesellschaft, Munich, Germany

[21] Appl. No.: 987,654

[22] Filed: Dec. 9, 1992

[51] Int. Cl.⁶ .............................................. A61B 17/56
[52] U.S. Cl. ........................................ 601/2; 607/51
[58] Field of Search ........ 128/24 AA, 660.03, 24 EL; 607/51, 50; 601/2, 3, 4

[56] References Cited

U.S. PATENT DOCUMENTS

| | | | |
|---|---|---|---|
| 4,526,168 | 7/1985 | Hassler et al. | 128/24 EL |
| 4,674,505 | 6/1987 | Pauli et al. | 128/24 EL |
| 4,875,487 | 10/1989 | Seppi | 128/660.03 |
| 4,905,671 | 3/1990 | Senge et al. | 128/24 AA |
| 4,928,672 | 5/1990 | Grasser et al. | 128/24 EL |
| 4,979,501 | 12/1990 | Valchanov et al. | 128/24 AA |
| 5,003,965 | 4/1991 | Talish et al. | 128/24 AA |
| 5,058,569 | 10/1991 | Hassler et al. | 128/24 EL |
| 5,191,880 | 3/1993 | McLeod et al. | 128/24 AA |
| 5,207,215 | 5/1993 | Rattner et al. | 128/24 EL |
| 5,209,221 | 5/1993 | Riedlinger | 128/24 EL |
| 5,211,160 | 5/1993 | Talish et al. | 128/24 AA |
| 5,233,972 | 8/1993 | Rattner | 128/240 EL |
| 5,309,897 | 5/1994 | Hassler et al. | 601/4 |

Primary Examiner—Krista M. Pfaffle
Attorney, Agent, or Firm—Hill, Steadman & Simpson

[57] ABSTRACT

The invention relates to a method for stimulating bone growth in a mammal. The method comprises the step of exposing a bone zone where bone growth is to occur to cavitation for bringing forth haemorrhage and/or microfissures and/or to at least partially loosened bone chips at said bone zone.

8 Claims, 1 Drawing Sheet

METHOD FOR THE MEDICAL TREATMENT OF PATHOLOGIC BONE

FIELD OF THE INVENTION

The invention relates to the medical treatment of bone pathology, e.g. delayed fracture healing, pseudoarthrosis etc., by applying acoustic energy to the site to be treated. More specifically the invention relates to a method for stimulating bone growth in a mammal by applying acoustic energy to a region of the bone where bone growth is to occur.

1. Description of the Prior Art

In a known method of this kind focussed shock waves are applied to the site to be treated. The intensity of the shock waves is such that haemorrhage occurs at the site to be treated (see U.S. Pat. No. 4,905,671). This method requires a high amount of acoustic energy to be applied to the patient.

2. Objects of the Invention

It is an object of the invention to develop a method for the medical treatment of bone pathology which allows for inducing bone growth at the site to be treated at low energy amounts. This and other objects of the invention will become evident from the following description of the invention.

SUMMARY OF THE INVENTION

The above object is achieved in a method for stimulation bone growth in a mammal comprising the step of exposing a bone zone where bone growth is to occur to cavitation for bringing forth at the bone zone to be treated at least one symptom of the group consisting of haemorrhage, microfissures and at least partially loosened bone chips. Due to cavitation in the tissue surrounding the bone zone to be treated, disruptive effects are exerted on the tiny blood vessels of the periosteum and the cortical bone below the periosteum. Cavitation in this region occurs at modest energy doses applied to the patient, so haemorrhage and/or microfissures and/or at least partially loosened bone chips can be induced at low energy amounts applied to the mammal. As is known from U.S. Pat. No. 4,905,671 haemorrhage at the treated bone zone leads to the formation of a so called fraction haematoma which is supposed to be the seed for bone growth. Inducing microfissures and/or at least partially loosening bone chips is also favourable for bringing forth bone growth.

Cavitation is preferably induced by applying acoustic energy to the bone zone to be treated. This can be, for instance, effected by applying acoustic rarefaction pulses to the bone zone to be treated, the rarefaction pulses having an intensity, i.e. an energy content, sufficient to bring forth at least one symptom of the above cited group of symptoms.

If rarefaction pulses are applied, it can be most useful to focus the rarefaction pulses. In this way cavitation is limited to the very site where treatment is to occur. Besides, by focussing the rarefaction pulses cavitation can be induced at even lower energy doses applied to the patient.

Cavitation at the bone zone to be treated can also be brought forth by applying a series of (positive) acoustic pressure pulses, e.g, shock waves, with a repetition frequency high enough to prevent the tissue surrounding the bone zone to be treated from recovering from the effect of the decrease of pressure following each pressure pulse. Cavitation is brought forth in this way by superposition of the cavitational effects due to the decrease of pressure of a plurality of successive pressure pulses.

BRIEF DESCRIPTION OF THE DRAWINGS

For a better understanding of the invention reference should be made to the accompanying drawings in which there is illustrated and explained a preferred embodiment of the invention.

DETAILED DESCRIPTION

Figure 1:
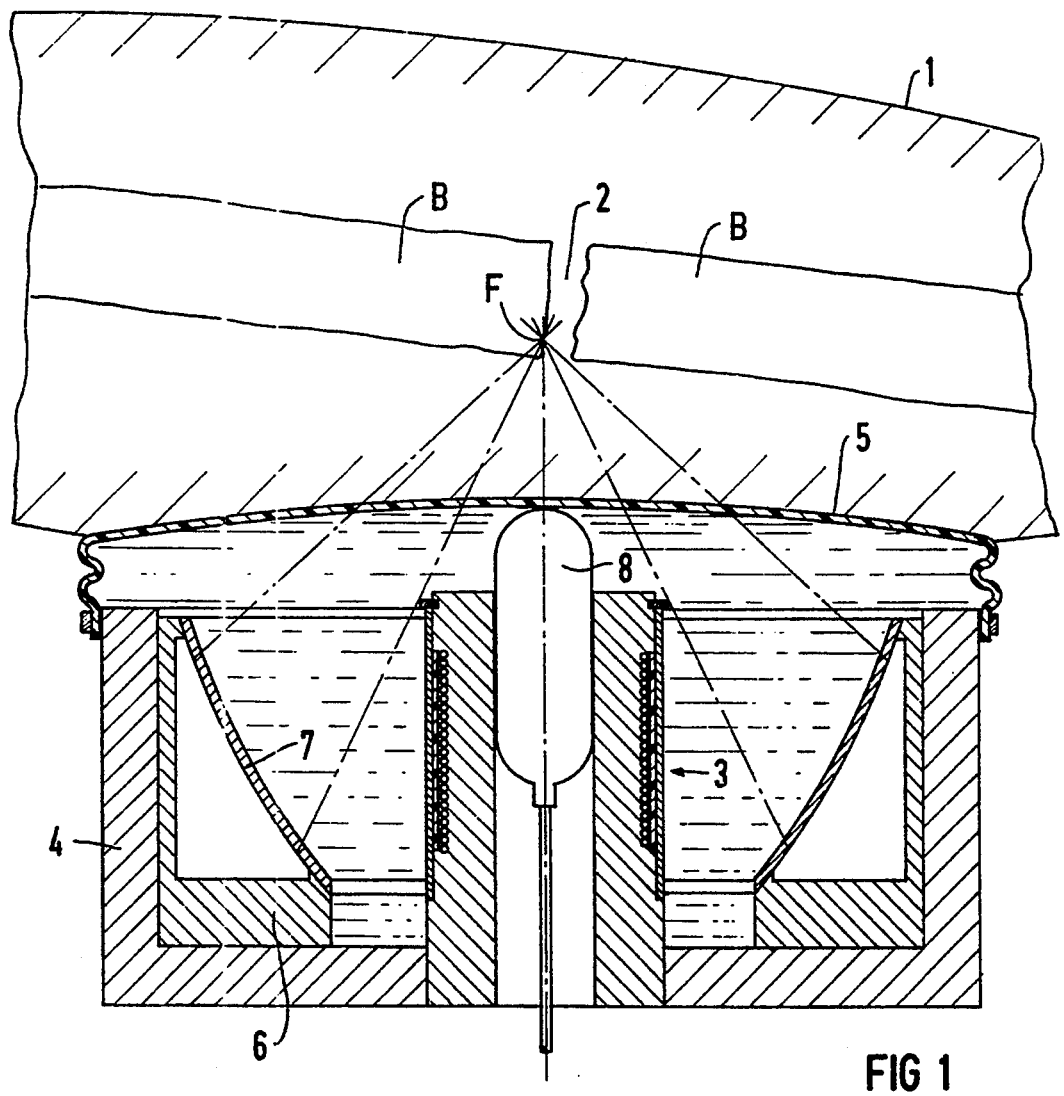
FIG. 1 shows an acoustic pulse generator for generating acoustic rarefaction pulses, applied to an arm with a fractured upper arm bone.

FIG. 1 shows an acoustic pulse generator for generating acoustic rarefaction pulses of the type described in detail in co-pending U.S. patent application Ser. No. 07/739,179, now U.S. Pat. No. 5,309,897, the disclosure of which is herewith incorporated by reference.

The generator serves the purpose of irradiating pathologic bone zones, for instance fractures, pseudoarthrosis etc., by exposing the pathologic bone zone to cavitation. In FIG. 1 an upper arm 1 is illustrated with an upper arm bone B having suffered a fracture 2.

The generator has central acoustic pulse source 3 which generates positive acoustic pressure pulses. These propagate radially outwardly in an liquid acoustic propagation medium contained in a housing 4 closed at its application end by a flexible application bellows 5.

The acoustic pulse source 3 is surrounded by a reflector 6 arranged inside housing 4 and having a reflecting surface 7 of parabolic shape. As the acoustic pulses emanating from the acoustic pulse source 3 are cylindrical wave pulses and as the acoustic pulse source 3 and the reflecting surface 7 have the same central axis, an acoustic pulse generated by the acoustic pulse source 3 is focussed by the reflector 6 to a focus zone outside bellows 5. The center of the focus zone is referenced F.

The reflector 6 is an acoustically soft reflector, i.e. the reflection of incident acoustic pulses occurs at a boundary surface to a medium which is acoustically soft compared to the acoustic propagation medium. The acoustic impedance of the medium having the boundary surface, thus is lower than that of the propagation medium. Reflector 6 therefore has a negative reflection factor. This means a positive acoustic pressure pulse emanating from pulse source 3 is refleced at the reflecting surface 7 as an acoustic rarefaction pulse, i.e. a negative pressure pulse, which is converged to the focus zone.

The generator is applied by means of application bellows 5 to upper arm 1 in a position such that the center F of the focus zone lies at the edge of fracture 2 on the left side of fracture 2. This achieved with the aid of an ultrasound locating system, known per se, the ultrasound applicator 8 of which is received in a central bore of the pulse source 3.

Figure 2:
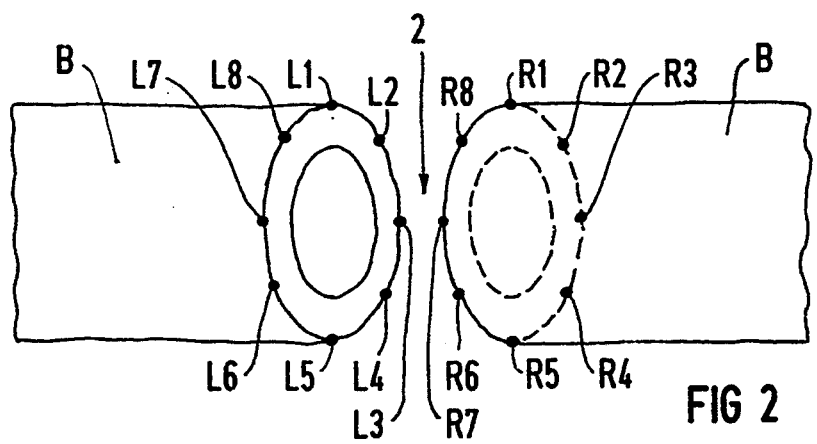
FIG. 2 shows the sites of the fracture of the upper arm bone at which rarefaction pulses are to be applied.

The generator and the upper arm 1 are displaced relative to each other for treatment of fracture 2 such that the focus zone of the rarefaction pulses is moved point by point along the edge of fracture 2 on each side of fracture 2. At each point of the movement at least one rarefaction pulse, preferably a series of rarefaction pulses, is applied to the edge of fracture 2. In FIG. 2 the points of the movement, i.e. the sites of rarefaction pulse application, are referenced R1 to R8 on the right and L1 to L8 on the left side of the fracture 2, respectively. If the upper arm bone B is aligned properly and the focus zone is sufficiently large, rarefaction pulses can be applied to corresponding sites on the left and right side of the fracture, e.g. sites L1 and R1, jointly.

The intensity of the rare faction pulses is such, that due to cavitation broght forth by these pulses, haemorrhage at the site of rarefaction pulse application occurs due to rupture of the small blood vessels of the periosteum and/or microfissures are induced and/or bone chips are at least partially loosend in the region of cortical bone situated below the periosteum. This results in the formation of a fracture haematoma which as well as microfissures and at least partially loosened bone chips is known to inducce bone growth even in the case of delayed bone consolidation.

Preferred peak pressure amplitude of the rarefaction pulses is about 100 bar (negative) though higher and even lower peak pressure amplitudes are possible.

The movement between generator and upper arm preferably is effected in a fashion such that points of rarefaction pulse application are separated from each other by a distance not greater than the respective dimension of that region of the focus zone within which the intensity of the rarefaction pulses is sufficient to induce haemorrhage and/or microfissures and/or to at least partially loosen bone chips.

Cavitation at the bone zone to be treated can also be brought forth by applying to the site to be treated a series of (positive) acoustic pressure pulses, e.g. shock waves, with a repetition frequency high enough to prevent the tissue surrounding the bone zone to be treated from recovering from the effect of the decrease of pressure following each pressure pulse. Cavitation is brought forth in this way by superposition of the cavitational effects due to the decrease of pressure of a plurality of successive pressure pulses.

The pressure pulses are preferably focussed for the same reasons as in the case of the rarefaction pulses. The repetition frequency is at least 3 Hz, preferably at least 10 Hz.

The generator for generating the pressure pulses can be constructed just the same as the generator for generating the rarefaction pulses described above, with the sole exemption that an acoustically hard reflector is used. A pressure pulse generator of this type is described in U.S. Pat. No. 5,058,569, the disclosure of which is herewith incorporated by reference. Also incorporated by reference are the disclosures of U.S. Pat. Nos. 4,674,505 and 4,928,672, in which a further type of generator for generating acoustic pressure pulses is described.

Acoustic rarefaction pulses can also be generated, for instance, by applying an electric current pulse of suitable polarity to a piezoelectric pressure pulse generator of the type disclosed in U.S. Pat. No. 4,526,168, the disclosure of which is herewith incorporated by reference.

Cavitation can also be induced by exciting an ultrasound wave source to periodical oscillation for generating ultrasound waves having both positive and negative half cycles and applying the generated ultrasound waves to the site to be treated. Cavitation will then occur during the negative half cycles.

To prevent the bone and the surrounding tissue at the site to be treated from becomming heated by the ultrasound waves to physiologically unsuitable temperatures the ultrasound waves may be generated in the form of so called ultrasound bursts, with each burst comprising at least one, normally a plurality of cycles and being separated from the following burst by a period of time during which no ultrasound emission occurs. Thus, it is possible to apply ultrasound of high intensity during the bursts and nevertheless keeping the overall intensity of ultrasound at a physiologically tolerable level.

As ultrasound wave source conventional piezoelectrical transducers may be used.

While the invention has been decribed in terms of a preferred embodiment, those skilled in the art will appreciate that various modifications, substitutions, omissions and changes may be made without departing from the spirit thereof. Accordingly, it is intended that the scope of the invention be limited solely by the scope of the following claims.

What I claim is:

1. A method for stimulating bone growth in a mammal comprising the step of applying acoustic rarefaction pulses to a bone zone where bone growth is to occur, said step of applying generating at said bone zone and producing at least one symptom of the group consisting of haemorrhage, microfissures and at least partially loosened bone chips at the bone zone.

2. The method of claim 1, further comprising the step of focussing said rarefaction pulses on the bone zone.

3. A method for stimulating bone growth in a mammal comprising the step of applying a series of positive acoustic pressure pulses each followed by a decrease of pressure to a bone zone where bone growth is to occur, said step of applying generating at said bone zone and producing at least one symptom group consisting of haemorrhage, microfissures and at least partially loosened bone chips, said series of positive acoustic pressure pulses having a repetition frequency for superimposing cavitational effects at said bone zone due to the decrease of pressure of a plurality of successive ones of said pressure pulses.

4. The method of claim 3, wherein said repetition frequency is at least 3 Hz.

5. The method of claim 3, further comprising the step of focussing said series of pressure pulses on the bone zone.

6. The method of claim 3 wherein said repetition frequency is at least 10 Hz.

7. A method for stimulating bone growth in a mammal comprising the step of applying ultrasound waves having both positive and negative half cycles to a bone zone where bone growth is to occur, said step of applying generating cavitation at said bone zone and producing at least one symptom of the group consisting of haemorrhage, microfissures and at least partially loosened bone chips.

8. The method of claim 7, wherein the step of applying said ultrasound waves is further defined by applying said ultrasound waves in the form of ultrasound bursts, each burst comprising at least one cycle of said ultrasound wave.

* * * * *